United States Patent

Brown et al.

[11] Patent Number: 5,808,161
[45] Date of Patent: Sep. 15, 1998

[54] PROCESS FOR THE PRODUCTION OF DIISOPROPYL ETHER AND ISOPROPANOL EMPLOYING A SOLVENT

[75] Inventors: Stephen H. Brown, Princeton, N.J.; Jeffrey C. Trewella, Kennett Square, Pa.

[73] Assignee: Mobil Oil Corporation, Fairfax, Va.

[21] Appl. No.: 567,389

[22] Filed: Dec. 4, 1995

[51] Int. Cl.⁶ .............................. C07C 41/00; C07C 29/00
[52] U.S. Cl. ........................ 568/694; 568/671; 568/840
[58] Field of Search ........................ 568/671, 697, 568/694, 895, 897, 840

[56] References Cited

U.S. PATENT DOCUMENTS 5,118,871 6/1992 Cikut .
5,324,865 6/1994 Beech .
5,600,023 2/1997 Marker et al. .

Primary Examiner—Gary Geist
Assistant Examiner—Karl J. Puttlitz, Jr.
Attorney, Agent, or Firm—Thomas W. Steinberg; Malcolm D. Keen

[57] ABSTRACT

A process has been discovered to employ an inert or unreactive solvent in the liquid phase process for production of isopropyl alcohol and diisopropyl ether from a propylene-rich hydrocarbon feedstream and water where the process is carried out in contact with acidic aluminosilicate catalyst particles. When an inert solvent is used, oxygenates production is enhanced and catalyst productivity is substantially increased.

13 Claims, 2 Drawing Sheets

PROCESS FOR THE PRODUCTION OF DIISOPROPYL ETHER AND ISOPROPANOL EMPLOYING A SOLVENT

FIELD OF THE INVENTION

This invention relates to a process for the production of ethers and/or alcohols from light olefins and water. The invention particularly relates to a fixed bed process for the production of high octane value diiopropyl ether and isopropyl alcohol by hydration of propylene in a single liquid hydrocarbon phase employing zeolite or resin catalyst. The invention especially relates to a method for promoting propylene hydration and ether formation by using an unreactive solvent in the process which increases oxygenate productivity.

BACKGROUND OF THE INVENTION

The need to eliminate lead-based octane enhancers in gasoline has provided incentive for the development of processes to produce high octane gasolines blended with lower aliphatic alkyl ethers as octane boosters. Oxygenates such as lower molecular weight alcohols and ethers, particularly isopropanol (IPA) and diisopropyl ether (DIPE) are in the gasoline boiling range and are known to have high blending octane numbers. In addition, by-product propylene from which IPA and DIPE can be made is usually available in a fuels refinery. An important aspect of research in the petroleum industry relates to processes to produce high octane lower aliphatic alkyl ethers as octane boosters and supplementary fuels from readily available fuels refinery streams.

Adapting available refinery feedstock to produce these oxygenates as octane enhancers involves two steps: olefin hydration and etherification. For the conversion of propylene feedstock, the preferred octane booster product is DIPE since the water solubility of IPA can introduce new and troublesome problems were it to be used in quantity as a fuels octane booster. Hence, artisans in the field have vigorously pursued new methods to facilitate the conversion of propylene to IPA simultaneously with the conversion of IPA to DIPE.

The catalytic hydration of olefins, particularly $C_3$ and $C_4$ olefins, to provide alcohols and ethers is a well-established art. Representative olefin hydration processes are disclosed in U.S. Pat. Nos. 2,262,913; 2,477,380; 2,797,247; 3,798,097; 2,805,260; 2,830,090; 2,861,045; 2,891,999; 3,006,970; 3,198,752; 3,810,848; 3,989,762, among others.

Olefin hydration employing medium pore and large pore zeolite catalyst is a known synthesis method. As disclosed in U.S. Pat. No. 4,214,107 (Chang et al.), lower olefins, in particular propylene, are catalytically hydrated over a crystalline aluminosilicate zeolite catalyst having a silica to alumina ratio of at least 12 and a Constraint Index of from 1 to 12, e.g., acidic ZSM-5 type zeolite, to provide the corresponding alcohol, essentially free of ether and hydrocarbon by-product. Acid resin catalysts such as Amberlyst 15 may also be used for hydration of light olefins.

The production of ether from secondary alcohols such as isopropanol and light olefins is known. As disclosed in U.S. Pat. No. 4,182,914, DIPE is produced from IPA and propylene in a series of operations employing a strongly acidic cationic exchange resin as catalyst. Recently, processes for the hydration of olefins to provide alcohols and ethers using zeolite catalyst such as ZSM-5 or zeolite Beta have been disclosed in U.S. Pat. Nos. 4,214,107 and 4,499,313 to Bell et al.; and U.S. Pat. Nos. 4,757,664, 4,857,664 and 4,906,187 to T. Huang. These patents are incorporated herein in their entirety by reference. One of the advantages in using zeolite catalyst for hydration and/or etherification of light olefins is the regenerability of the catalyst. Where resin based catalysts can decompose at the high temperatures required to remove deactivating amounts of carbonaceous deposits, zeolite catalysts remain thermally stable and can be regenerated oxidatively or in contact with hydrogen.

The hydration and etherification of lower olefins such as propylene to produce IPA and DIPE over a fixed bed of shape selective zeolite catalyst is generally carried out in liquid phase employing a feedstream comprising water and propylene at temperatures in excess of 200° F. and high pressure, preferably above 1000 psi (7000 kPa). While attempting to maximize the rate of conversion, process conditions are selected to also reduce the more disadvantageous reactions which can occur during the process that could compromise the process advantages. These adverse reactions include the oligomerization of propylene, the reversible formation of deactivating amounts of coke and carbonaceous deposits on the catalyst and the irreversible hydrothermal attack of water on the catalyst. These adverse reactions tend to find favor with increasing temperature and concentration providing a challenging limit to workers in the field with respect to reactor temperature. Consequently, an improvement in catalyst productivity leading to enhanced oxygenate production with all the attendant benefits of equipment downsizing and cost reduction has remained a research target of great importance.

An objective of the present invention is the development of an improved process for the production of IPA and DIPE wherein oxygenate production and catalyst stability are substantially increased.

A specific objective of the invention is to provide a liquid phase DIPE production process employing inert solvents to enhance catalyst productivity and activity.

SUMMARY OF THE INVENTION

A unique process has been discovered for the production of DIPE and IPA from propylene that results in a surprising increase in catalyst productivity and a consequent increase in oxygenates production. The improvement in DIPE production is achieved by avoiding the formation of an aqueous liquid phase in the fixed bed catalytic DIPE process. An aqueous liquid phase promotes irreversible aging and deactivation of acidic zeolite catalysts that have been found to be most effective in the DIPE production process. The irreversible catalyst aging reaction has been substantially reduced by employing an inert or unreactive co-solvent in the process to supplement the solvent properties of IPA which is formed by propylene hydration and typically recycled in the liquid phase fixed bed reaction zone.

More particularly, the invention comprises a liquid phase process exhibiting high catalyst productivity for the production of diisopropyl ether and isopropanol by hydration and etherification of a fresh olefinic feedstream rich in propylene and containing water. The process comprises the steps of introducing the feedstream in combination with an inert solvent into a liquid phase olefin etherification and hydration fixed bed reaction zone or zones in contact with solid acidic metallosilicate catalyst particles under olefin hydration and etherification conditions. An effluent stream is recovered from the reaction zone comprising said isopropanol, diisopropyl ether, inert solvent and water. The effluent stream is separated to recover diisopropyl ether, isopropanol, inert solvent and water. The process can include recycling of isopropanol, inert solvent and water to the reaction zone.

The inert solvent most useful in the process of the invention are selected from those solvents that are miscible in hydrocarbons and water and have a boiling point below the boiling point of water. A preferred solvent is para dioxane (p-dioxane).

DETAILED DESCRIPTION OF THE INVENTION

Figure 1:
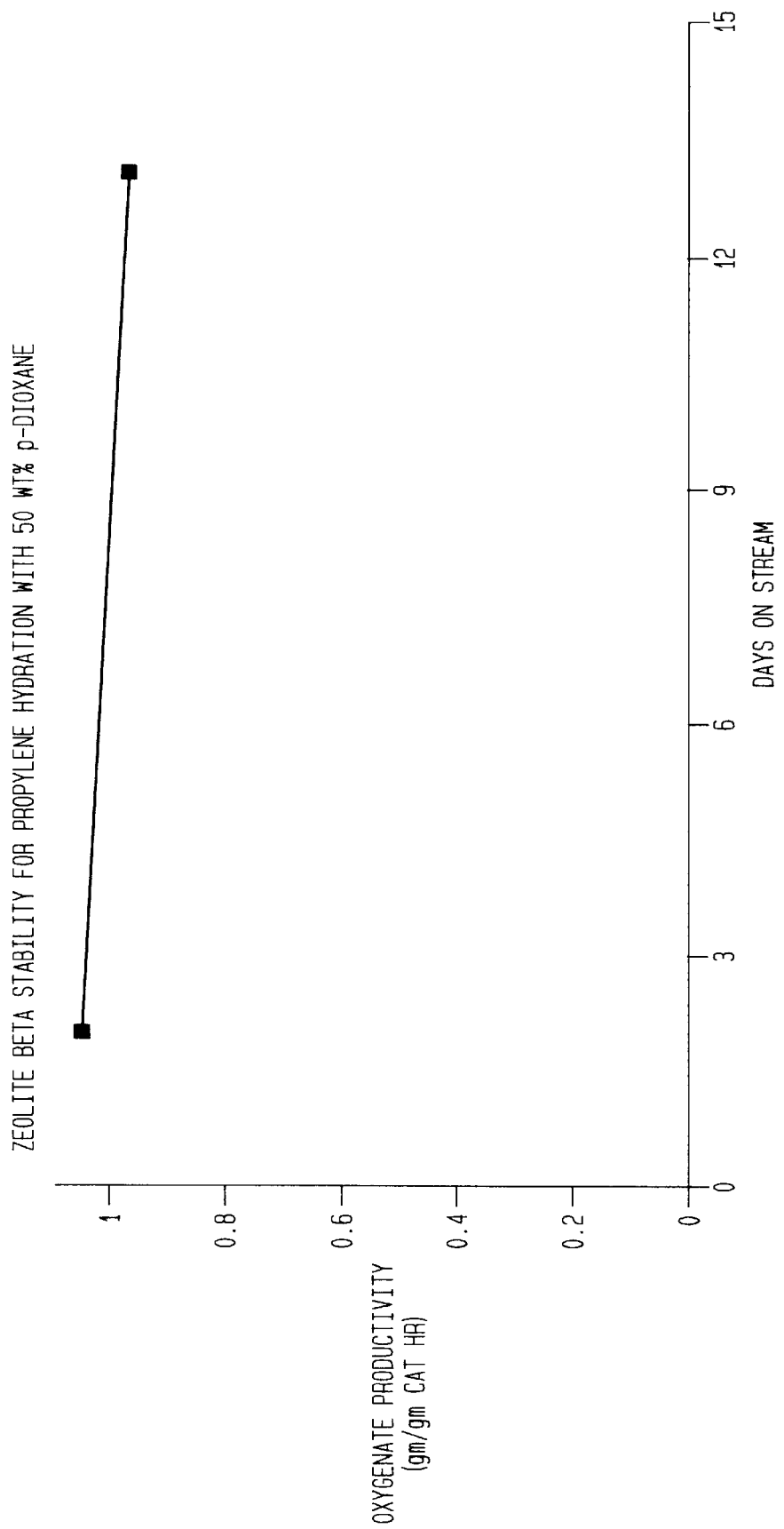
FIG. 1 is a graph illustrating the stability of zeolite Beta catalyst for propylene hydration according to the process of the invention.

The process of the instant invention embodies a sharp departure from known technology as evident by the unexpectedly superior performance of the novel process described hereinafter. Nevertheless, elements of the prior art such as catalysts employed and reaction conditions are utilized in the invention. Art related conditions for reaction temperature, pressure ranges, zeolite catalysts and weight hourly space velocities such as described in U.S. Pat. No. 5,138,102 to Beech, et al. are applicable to the present invention except that the invention described herein reveals the unexpected process benefits of carrying out propylene hydration and etherification in the presence of a solvent.

As known in the art, the olefins hydration and etherification process is depicted in simplified form as comprising the reaction of propylene with water catalyzed by strong acid to form isopropanol. Reaction may be allowed to continue in the hydration zone to form diisopropyl ether (DIPE). The operating conditions of the olefin hydration and etherification reaction step include a temperature of about 50° to 450° C., preferably from 100° to 250° C. and most preferably from 120° to 220° C. The total pressure is about 700 to 24000 kPa (100 to about 3500 psi, preferably 500–2000 psi). Water to olefin reactant concentrations are maintained at mole ratios of about 0.1 to 30, preferably 0.1 to 5.

The preferred catalytic methods known in the art for making DIPE employ porous solid acid catalysts, such as zeolites Beta, Y, ZSM-35 and/or MCM-22 aluminosilicate. The preferred hydration/etherification catalyst comprises acidic, shape selective porous zeolite having a pore size of about 5–8 Angstroms, such as aluminosilicate zeolite Beta. Also, MCM-22, having pores similar to zeolite Beta and ZSM-5 are known for etherification catalysis, as disclosed by Marler et al. in U.S. Pat. No. 5,105,023.

DIPE etherification conditions may vary widely in choice of temperature, pressure and reaction time. The preferred method reacts propene with water in an adiabatic downflow reactor containing a fixed bed of catalyst, such as zeolite Beta, at 100° to 250° C. and pressure of at least 4000 kPa. However, it is understood that the unit operations described herein can be conducted with any number of specific process steps within the skill of the art.

The olefin hydration and etherification reaction step is carried out in liquid phase or supercritical dense phase in a continuous manner using a fixed bed flow reactor. Weight hourly space velocity based on catalyst weight is maintained in the range of 0.1 to 10/hour when operating continuously.

Various modifications can be made within the inventive concept, especially with regard to reactor system configuration. Although a single reactor bed may be employed, it is advantageous to employ a series of fixed bed reactor units to permit adequate control of reaction conditions, especially temperature, phase behavior and flow parameters. It is ordinarily desirable to recover any unreacted olefin and recycle it to the reactor. Unconverted isopropanol recovered from the final reactor effluent may also be recycled advantageously for further conversion to ether.

Catalyst stability is a challenging issue in the propylene hydration process employing zeolite catalysis. Both reversible (coking) and irreversible (dealumination or desulfonation) aging have been demonstrated to occur during DIPE synthesis. IPA addition, either by reactor pumparound or IPA recycle, mitigates both problems because IPA reduces the tendency of the reaction mixture to form separate phases. Controlling the phases during propylene hydration is required to maintain activity, stability, and selectivity. Phase control is implemented by maintaining a single liquid hydrocarbon phase using pumparound, high pressure, and extinction IPA recycle. Because IPA is a product of an equilibrium-limited system, propylene hydration would be inhibited if the full capabilities of IPA to inhibit oligomerization and control the reaction phase were utilized alone.

It has been discovered that the use of an inert solvent with or without IPA recycle overcomes the foregoing challenges and provides the following benefits:

Oxygenate productivity is increased nearly three-fold;

Stability is improved about 50-fold because the solvent keeps the reactants in a single liquid hydrocarbon phase;

Minimal additional capital is required because the solvent can be extracted with IPA and recycled;

Process flexibility is improved as the water to propylene mole ratio can be varied over a large range (i.e., from 0.1 to 1.0).

The reaction conditions of the present invention vary in some respects from the prior art, although the present process utilizes the same catalysts. A series of experiments was carried out to compare the performance of the liquid phase process of the instant invention using p-dioxane as a solvent with zeolite Beta as catalyst under essentially the same conditions as employed heretofore in the preferred art in liquid phase fixed bed reactors. The reaction conditions, feed compositions and results in terms of product selectivity and productivity are presented in Table 1. Examples 1 and 3 represent the process of the invention that includes a solvent while Examples 2, 4 and 5 are processes of close prior art that do not include a solvent.

TABLE 1

| | Comparison with Prior Work at 1000 psi | | | | |
|---|---|---|---|---|---|
| Example | 1 | 2 | 3 | 4 | 5 |
| HOS | 22 | 40 | 42 | 53.0 | 162 |
| Temperature (°F.) | 300 | 300 | 320 | 330 | 330 |
| $H_2O/C_{3=}$ (a) | 0.56 | 1.0 | 0.52 | 0.5 | 0.5 |
| Feed Composition (wt %) | | | | | |
| Propylene | 39 | 69.3 | 40 | 82.1 | 79.6 |
| $H_2O$ | 10 | 3.07 | 9 | 17.9 | 20.4 |
| p-dioxane | 51 | — | 51 | — | — |
| Propylene WHSV | 0.73 | 0.40 | 1.54 | 0.40 | 0.40 |
| Product Comp. (wt %) (b) | | | | | |
| Propylene | 37.6 | 40.7 | 40.0 | 45.2 | 34.2 |
| Water | 5.2 | 22.5 | 5.0 | 8.3 | 7.7 |
| IPA | 28.5 | 15.0 | 30.2 | 18.5 | 24.0 |

TABLE 1-continued

| | Comparison with Prior Work at 1000 psi | | | | |
|---|---|---|---|---|---|
| Example | 1 | 2 | 3 | 4 | 5 |
| DIPE | 28.0 | 20.6 | 23.9 | 26.6 | 31.4 |
| Oligomer | 0.7 | 1.2 | 0.8 | 1.4 | 2.8 |
| Productivity (c) | 0.73 | 0.25 | 1.48 | 0.35 | 0.34 |

(a) - $H_2O$/propylene mole ratio
(b) - normalized to exclude p-dioxane
(c) - gm oxygenates/gm zeolite hr Referring now to FIG. 1, the figure illustrates the stability of zeolite Beta catalyst at 320° F., 1000 psig, and a feedstock of 50 wt % p-dioxane, 40 wt % propylene, and 10 wt % water ($H_2O$/propylene mole ratio=0.52). Without p-dioxane, a 20% water+80% propylene feedstock (water/propylene mole ratio=0.52) completely deactivates after seven days. It would take well over a year to completely deactivate the p-dioxane system. In current designs a similar stability can be achieved by using pumparound and extinction IPA recycle. However, in view of the fact that recycled IPA participates in these equilibrium-controlled reactions, these strategies of pumparound and/or IPA recycle limit oxygenate productivity.

Figure 2:
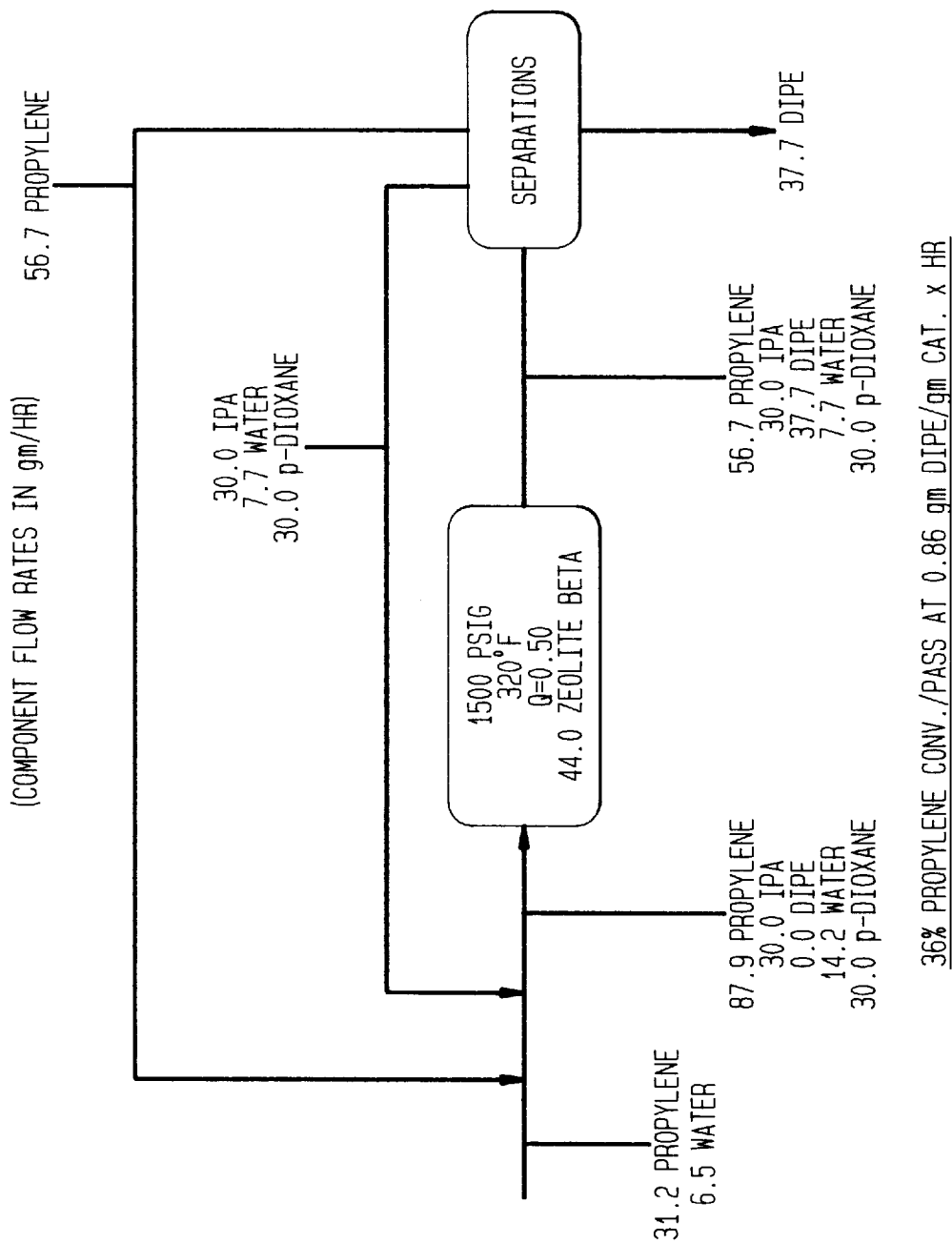
FIG. 2 is a process flow diagram of the process of the invention.

Referring now to FIG. 2, a process flow diagram is shown indicating the improved activity of the process of the invention (0.86 vs. 0.20 gm DIPE/gm cat×hr) and selectivity (95% vs. 90% DIPE) compared to known zeolite-catalyzed, liquid phase IPA/DIPE production. Neither p-dioxane nor IPA are either created or converted but are recycled.

In the presence of an inert solvent, productivity remains constant at near 1 gm of oxygenates/gm catalyst/hr, past an 80% approach to equilibrium. For the IPA/DIPE production process, water is both a reactant and a catalyst inhibitor. So as reactant water is consumed in the process of the invention, water acting as catalyst inhibitor is reduced. The insensitivity of catalyst activity to approach to equilibrium indicates that the increase in activity due to poison removal offsets the normal drop in productivity associated with approaching equilibrium when the process is carried out in the presence of an inert solvent.

p-Dioxane can be used to either replace (Table 1) or supplement (FIG. 2) IPA recycle. The illustrated process flow diagram (FIG. 2 uses only 18 wt % p-dioxane, one third the amount used in the unit trials of Table 1. Much of the para-dioxane can be replaced with IPA recycle. Of course, as the artisan knows very well, pumparound can be added to the design to control the reaction exotherm without changing the key features of the invention.

Activity, stability, selectivity, and flexibility of the current art for zeolite catalyzed DIPE production processes can all be improved by addition of p-dioxane or other inert solvents. Because p-dioxane has such similar properties to IPA, it will also be recycled by the current design and therefore can be implemented at minimal additional capital and operating expense. The use of an inert solvent significantly improves the commercial potential of DIPE synthesis as a motor fuel oxygenate.

The process of the instant invention can also be utilized for the synthesis of specialty alcohols from C4+olefins and water. Employing the inert solvents and catalysts of the present invention higher molecular weight secondary alcohols can be prepared by the reaction of $C_4$+olefins and water. Higher molecular weight alcohols are difficult to synthesize due to the difficulty of mixing the non-polar olefins with water. These alcohols have potential uses for synthesis of detergents, lubricants, and other high volume specialty chemicals.

An optimal inert solvent for DIPE synthesis will have all of the following characteristics:

Miscible in both water and hydrocarbon.
Stable to acid, reactants, and products up to 400° F.
Boil near but not above 212° F. at 1 atm.

Solvents that are completely miscible in both reactants will best promote mixing, the primary objective. In order to be of any practical value, the solvent must be unreactive, i.e., inert, to avoid the cost of continuous addition of solvent and of separation and disposal of the solvent reaction products.

The ideal boiling point requirement is set by two conflicting needs. In propylene hydration, equilibrium conversion is favored by increasing the pressure. Use of a high boiling inert solvent minimizes its partial pressure in the system and therefore reduces the overall unit pressure requirement for a target hydration equilibrium. However, if the solvent is not more volatile than water, it cannot be conveniently separated. After aqueous extraction, it is important that the solvent distill overhead in a mixed azeotrope with IPA and water in order to avoid the large energy cost of vaporizing all the extraction water to recover the solvent.

In addition to the preferred p-dioxane, other useful solvents include sulfolane, dimethyl ether, tetrahydrofuran, 1,3-dioxane and alkyl ethers of ethylene glycol.

The preferred catalysts for making DIPE according to the process of the invention employ porous solid acid catalysts, such as zeolites Beta, Y, ZSM-35 and/or MCM-22 aluminosilicate. Acidic resins such as Amberlyst-15 can also be used as catalyst for the process of the invention. The preferred hydration/etherification catalyst comprises acidic, shape selective porous zeolite having a pore size of about 5–8 Angstroms, such as aluminosilicate zeolite Beta. Also, MCM-22, having pores similar to zeolite Beta and ZSM-5, is known for etherification catalysis, as disclosed by Marler et al. in U.S. Pat. No. 5,105,023. In addition to the foregoing materials, the zeolite employed herein can be composited with a porous matrix material such as carbon, alumina, titania, zirconia, silica, silica-alumina, silica-magnesia, silica-zirconia, silica-thoria, silica-beryllia, silica-titania, etc., as well as ternary oxide composition, such as silica-alumina-thoria, silica-alumina-zirconia, silica-alumina-magnesia, silica-magnesia-zirconia, etc.. The matrix can be in the form of a cogel. The relative proportions of zeolite component and matrix material, on an anhydrous basis, can vary widely with the zeolite content ranging from between 1 to about 99 wt %, and more usually in the range of about 5 to about 90 wt % of the dry composite.

What is claimed is:

1. A liquid phase process exhibiting high productivity for the production of diisopropyl ether and isopropanol by hydration and etherification of a fresh olefinic feedstream rich in propylene and containing water, said process comprising the steps of:

introducing said feedstream in combination with an inert solvent selected from the group consisting of p-dioxane, 1,3-dioxane, dimethyl ether, tetrahydrofuran, sulfolane and dialkyl ethers of ethylene glycol, into a liquid phase olefin etherification and hydration fixed bed reaction zone in contact with solid acidic catalyst particles under olefin hydration and etherification conditions;

recovering an effluent stream from said reaction zone comprising said isopropanol, diisopropyl ether, inert solvent and water; and separating said effluent stream to recover said diisopropyl ether, isopropanol, inert solvent and water.

2. The process of claim 1 including the further step of recycling one or more of said isopropanol, inert solvent and water to said reaction zone.

3. The process of claim 1 wherein said catalyst particles comprise solid, shape selective aluminosilicate particles.

4. The process of claim 3 wherein said aluminosilicate particles are selected from the group consisting of zeolite Beta, zeolite Y, ZSM-35 and MCM-22.

5. The process of claim 1 wherein said catalyst comprises zeolite Beta impregnated with zirconium oxide.

6. The process of claim 1 wherein said catalyst particles comprise acidic resin catalyst.

7. The process of claim 1 wherein said hydration and etherification conditions comprise a temperature of 50° to 450° C., pressure of 100 to 3,500 psi and water to olefin mole ratios of 0.1 to 30.

8. The process of claim 7 wherein said etherification conditions comprise temperature of 120° to 220° C., pressure of 500 to 2,000 psi and water to olefin mole ratio of 0.1 to 5.

9. In a liquid phase process for the hydration and etherification of a hydrocarbon feedstream rich in propylene and containing water to produce oxygenates comprising isopropanol and diisopropyl ether in a fixed bed reaction zone in contact with acidic aluminosilicate zeolite catalyst particles under olefin hydration and etherification conditions wherein a portion of the reaction zone effluent containing isopropanol is recycled to the reaction zone as reactant and solvent, the improvement comprising:

introducing an inert solvent selected from the group consisting of p-dioxane, 1,3-dioxane, dimethyl ether, tetrahydrofuran, sulfolane and dialkyl ethers of ethylene glycol into said liquid phase propylene etherification and hydration fixed bed reaction zone under said olefin hydration and etherification conditions;

recovering an effluent stream from said reaction zone comprising said isopropanol, diisopropyl ether, inert solvent and water;

separating said effluent stream to recover said diisopropyl ether, isopropanol, inert solvent and water; and recycling said isopropanol, inert solvent and water to said reaction zone, whereby catalyst productivity is enhanced and the diisopropyl ether production increased.

10. The process of claim 9 wherein said aluminosilicate particles are selected from the group consisting of zeolite Beta, zeolite Y, ZSM-35 and MCM-22.

11. The process of claim 1 wherein said hydration and etherification conditions comprise a temperature of 50° to 450° C., pressure of 100 to 3,500 psi and water to olefin mole ratios of 0.1 to 30.

12. The process of claim 9 wherein said catalyst productivity, i.e., grams of said oxygenates/gm catalyst/hour, is at least doubled over said hydration and etherification carried out in the absence of inert solvent.

13. A liquid phase process exhibiting high catalyst productivity for the production of $C_4+$ secondary alcohols by hydration of a fresh $C_4+$ olefinic feedstream containing water, said process comprising the steps of:

introducing said feedstream in combination with an inert solvent selected from the group consisting of p-dioxane, 1,3-dioxane, dimethyl ether, tetrahydrofuran, sulfolane and dialkyl ethers of ethylene glycol into a liquid phase olefin hydration fixed bed reaction zone in contact with solid acidic catalyst particles under $C_4+$ olefin hydration conditions;

recovering an effluent stream from said reaction zone comprising said $C_4+$ secondary alcohols, inert solvent and water; and separating said effluent stream to recover said $C_4+$ secondary alcohols.

* * * * *

UNITED STATES PATENT AND TRADEMARK OFFICE
CERTIFICATE OF CORRECTION

PATENT NO. : 5,808,161
DATED : September 15, 1998
INVENTOR(S) : Stephen H. Brown; Jeffrey C. Trewella It is certified that error appears in the above-identified patent and that said Letters Patent are hereby corrected as shown below:

Claims:

column 6, line 58, delete "sulfolane".
    column 7, line 32, delete "sulfolane".
    column 8, line 27, delete "sulfolane".

Signed and Sealed this

Twenty-third Day of February, 1999

Attest:

Q. TODD DICKINSON

*Attesting Officer*     Acting Commissioner of Patents and Trademarks